(12) United States Patent
Pardue et al.

(10) Patent No.: US 6,418,799 B1
(45) Date of Patent: Jul. 16, 2002

(54) SAMPLING APPARATUS

(75) Inventors: Bradley D. Pardue, Blaine; Raymond E. Garvey, Loudon, both of TN (US)

(73) Assignee: CSI Technology, Inc., Wilmington, DE (US)

( * ) Notice: Subject to any disclaimer, the term of this patent is extended or adjusted under 35 U.S.C. 154(b) by 0 days.

(21) Appl. No.: 09/357,468

(22) Filed: Jul. 20, 1999

(51) Int. Cl.⁷ .................................................. G01N 1/00
(52) U.S. Cl. ................................... 73/863.21; 73/863.23
(58) Field of Search .......................... 73/863.21, 863.23, 73/863.24, 863.25, 863.01, 863.11; 210/387, 459

(56) References Cited

U.S. PATENT DOCUMENTS

| | | | |
|---|---|---|---|
| 2,002,974 A | | 5/1935 | Bennett et al. |
| 2,334,802 A | | 11/1943 | Zuckermann |
| 2,390,539 A | | 12/1945 | Katcher |
| 3,203,253 A | | 8/1965 | Scheid |
| 3,267,723 A | | 8/1966 | Robinson |
| 3,268,077 A | | 8/1966 | Ball |
| 3,269,541 A | | 8/1966 | Neely |
| 3,386,580 A | | 6/1968 | Grabarczyk |
| 3,795,135 A | | 3/1974 | Andersen |
| 3,942,360 A | * | 3/1976 | Wada ............................ 73/61 |
| 4,038,189 A | | 7/1977 | Dison et al. |
| 4,047,814 A | | 9/1977 | Westcott |
| 4,055,498 A | | 10/1977 | Radnoti |
| 4,151,086 A | | 4/1979 | Brooks |
| 4,432,674 A | * | 2/1984 | Klose et al. ................... 406/19 |
| 4,504,397 A | | 3/1985 | Matthews |
| 4,704,911 A | | 11/1987 | Meloy |
| 4,826,597 A | * | 5/1989 | Silverwater et al. ........ 210/387 |
| 5,048,354 A | * | 9/1991 | Mullis, Sr. et al. ......... 73/863.25 |
| 5,239,861 A | | 8/1993 | Fuji et al. |
| 5,244,480 A | | 9/1993 | Henry |
| 5,531,129 A | * | 7/1996 | Thornton et al. ........... 73/863.24 |
| 5,853,445 A | | 12/1998 | Wong et al. |
| 5,942,700 A | * | 8/1999 | Radcliffe et al. ........... 73/863.24 |

FOREIGN PATENT DOCUMENTS

GB 2160 655 B 5/1989

* cited by examiner

Primary Examiner—Hezron Williams
Assistant Examiner—Charles D. Garber
(74) Attorney, Agent, or Firm—Luedeka, Neely & Graham PC

(57) ABSTRACT

A sampling apparatus is described which contains a cylindrical member containing first and second annular recesses on opposing sides thereof and an opening therethrough. At least one resilient sealing member is disposed in each of the recesses. At least one foraminous support disposed in the cylindrical member over the opening adjacent the first recess. A porous medium is adjacent the foraminous support between the foraminous support and the sealing member. A compression housing is provided which contains first and second housing members for compressing the cylindrical member, sealing members, foraminous support and porous medium between the first and second housing members and a clamping means for compressing the sealing members to form a fluid tight seal. A fluid sample is fed by means of a fluid inlet in the first housing member which inlet is in flow communication with the opening, porous medium and foraminous support. The fluid sample is also in flow communication with a fluid outlet in the second housing member. The clamping means is specially adapted to provide rapid insertion and removal of porous media from the sampling apparatus.

6 Claims, 4 Drawing Sheets

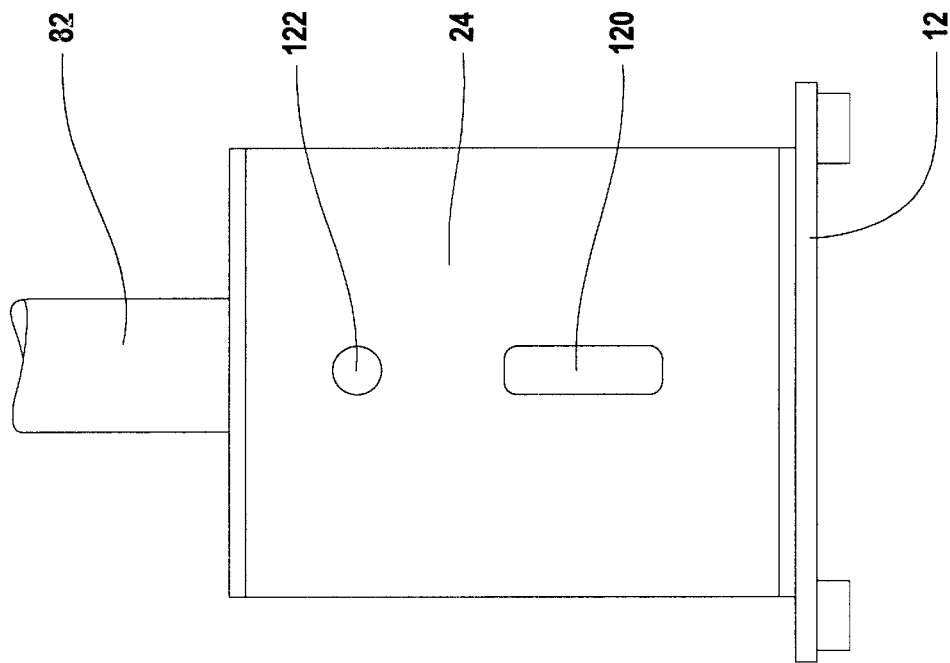
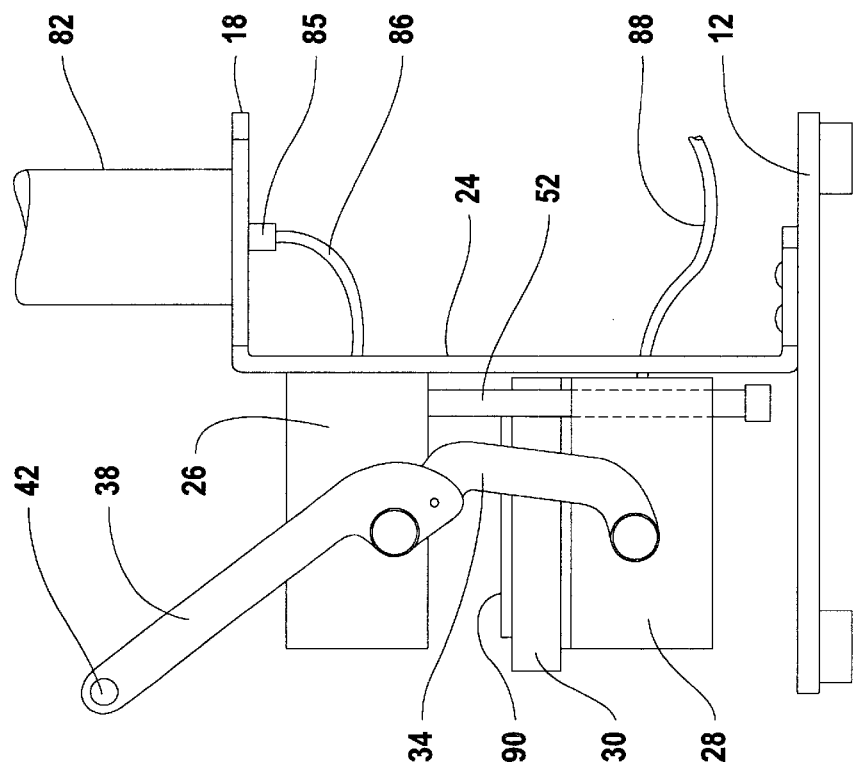

SAMPLING APPARATUS

FIELD OF THE INVENTION

The invention relates to an apparatus and method for making filter patch samples and for determining properties of particulates in a fluid.

BACKGROUND OF THE INVENTION

Rotating and reciprocating equipment is subject to failure before the economic life of the equipment has been reached due to a variety of reasons. One reason for premature failure is misalignment of the equipment causing excessive wear to moving parts. Another cause of failure is an increase in particulate material in fluids used to lubricate the moving parts of the equipment. Still another cause of failure is due to chemical changes in tile lubricating fluid compositions caused by moisture, excessive heat or other liquid contaminants.

Despite the advances made in tile field of lubricant analysis, there continues to be a need for the ability to precisely quantify the level and size distribution of particulate contaminants in lubricating fluids as well as identifying the particulates which may cause premature failure of the equipment so that corrective action can be taken at the earliest possible date. There is also a need for a relatively simple analytical device which can be used in a field setting to determine the quantity of contaminants and the size distribution thereof in an oleaginous fluid with a relatively high level of confidence.

SUMMARY OF THE INVENTION

The present invention provides an analytical device for determining various quantitative and qualitative properties of particulate contaminants in a fluid which is relatively simple and which can be used on a variety of fluids for particulate analysis thereof. In one aspect the invention provides a sampling apparatus which includes a compression housing containing first and second housing members. A filter media holder having opposed surfaces and having an opening therethrough is disposed between the first and second housing members. At least one resilient sealing member is disposed adjacent each of the surfaces of the holder for sealing between the holder and the first and second housing members. At least one foraminous support is adjacent at least one surface of the holder. A porous medium is disposed adjacent the foraminous support and a medium sealing member is adjacent the porous medium and the first housing member. A clamping means is attached to the first and second housing members for clamping the holder and sealing members between the first and second housing members for forming a fluid tight seal thereby defining a closed volume through which fluids may flow. The first housing member includes a fluid inlet which is in flow communication with the opening, porous medium and foraminous support. The second housing member includes a fluid outlet which is in flow Communication with the opening, porous medium and foraminous support, whereby a fluid flow path is formed from the inlet, through the porous medium and out the outlet for depositing particulates on the porous medium to thereby produce a sample of the particulates in the fluid.

In another aspect, the invention provides an optical sample preparation device which includes a fluid inlet reservoir connected in flow communication with an inlet port attached to a filter patch device. The filter patch device includes a cylindrical member containing first and second annular recesses on opposing sides thereof and an opening therethrough in flow communication with the inlet port. At least one resilient sealing member is disposed in each of the recesses. At least one foraminous support is disposed in the cylindrical member over the opening adjacent the first recess. At least one porous medium is disposed adjacent the foraminous support between the foraminous support and the sealing member. A compression housing containing first and second housing members maintains the cylindrical member, sealing member, foraminous support and porous medium in compression between the first and second housing members by use of a clamping means for compressing the sealing members to form a fluid tight seal. A fluid inlet in the first housing member is in flow communication with the inlet port, the opening, the porous medium and the foraminous support. A fluid outlet in the second housing member in flow communication with the opening, porous medium and foraminous support. A vacuum source is connected in flow communication with the field outlet for drawing a sample through the sample preparation device.

Another aspect of the invention provides a method for preparing a filter patch sample for optical analysis which includes providing an optical sample preparation device containing a fluid inlet reservoir connected in flow communication with an inlet port attached to a sampling apparatus according to the first aspect of the invention. According to the method, a fluid sample to be analyzed is fed to the fluid inlet reservoir of the sampling apparatus. A pressure is applied to the sample with the vacuum source to draw the fluid through the porous medium of the sampling apparatus. Upon drawing all of the fluid in the inlet reservoir through the sampling apparatus, a solvent or gas is flowed through the porous medium so as to remove residual fluid therefrom. Upon removal of residual fluid from the medium, the clamping means is unclamped in order to remove the porous medium from the medium holder.

Still another aspect of the invention provides a method for determining quantitative or qualitative properties of particulate solids in an oleaginous. material. The method includes providing an oleaginous fluid sample, feeding the fluid sample to a fluid sample holder having a defined volume in flow communication with a dual filter patch device containing first and second porous media, applying a reduced pressure to the filter patch device to draw tile fluid sample sequentially through the porous media, removing residual fluid sample from the porous media using a solvent for the fluid, and optically observing particulate material on the porous media.

The invention provides a compact, highly effective apparatus for obtaining filter patch samples for quantitative and/or qualitative analysis. The apparatus provides a liquid tight sealing means and may be used to provide multiple filter patch samples essentially simultaneously for determination of properties of contaminants having different particle sizes.

BRIEF DESCRIPTION OF THE DRAWINGS

Further features and advantages of the invention will become apparent by reference to the detailed description when considered in conjunction with the figures, which are not to scale, wherein like reference numbers indicate like elements through the several views, and wherein:

FIG. 8 is a side elevational view of a support frame and base for a sampling apparatus according to the invention; and FIG. 9 is a rear elevational view of a support frame and base for a sampling apparatus according to the invention.

DETAILED DESCRIPTION OF THE PREFERRED EMBODIMENTS

Figure 1:
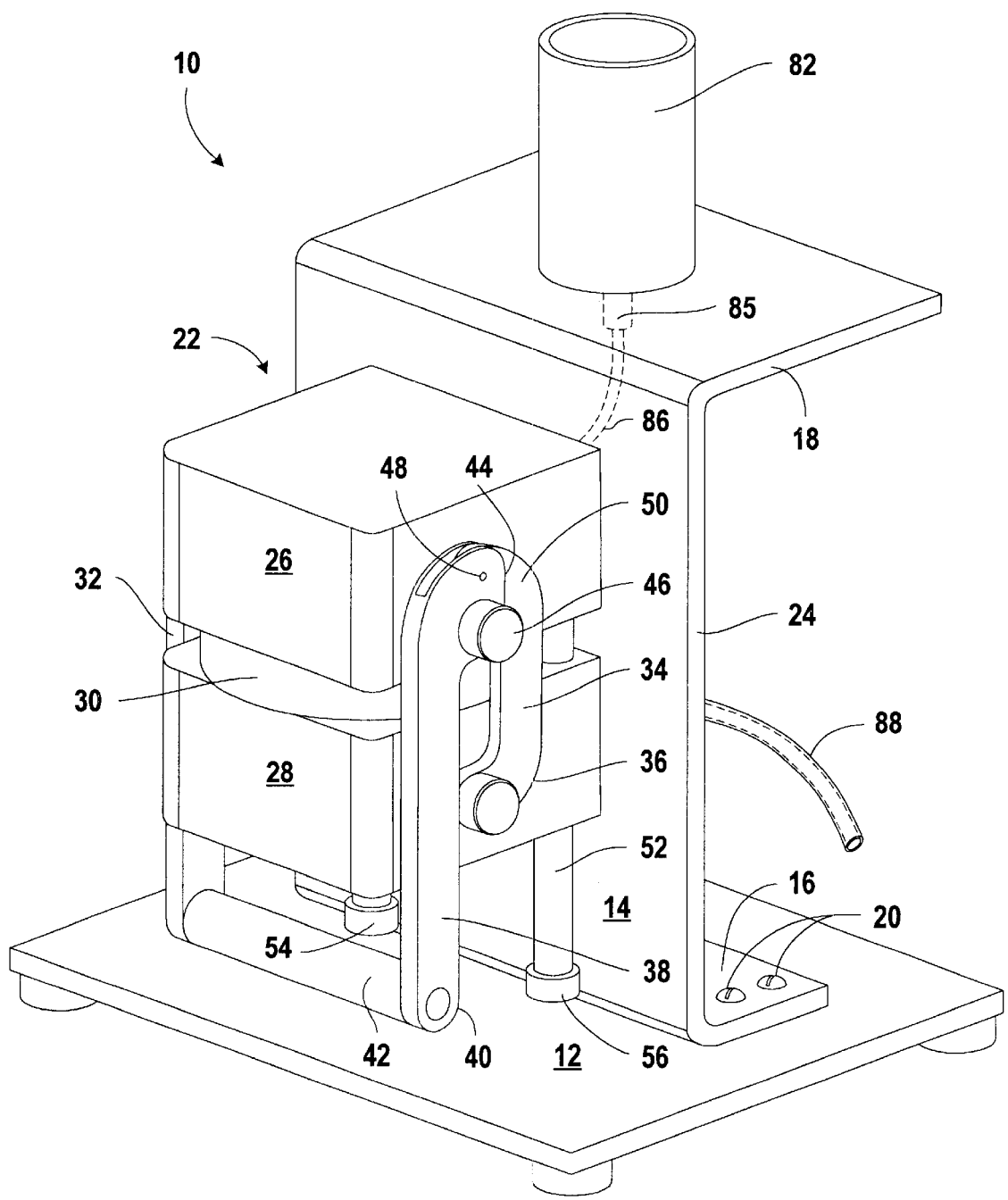
FIG. 1 is a perspective view, not to scale, of a sampling apparatus according to the invention.

In order to prepare one or more filter patches for determining quantitative and/or qualitative particulate contaminant in a liquid sample, a device 10 as shown in FIG. 1 is preferably used. The device 10 includes a support base 12 to which is attached a support frame 14 having two L-shaped sections 16 and 18. Section 16 is attached to the base 12 by means of attachment devices 20 such as bolts, screws, adhesives, welding and the like. The frame 14 and base 12 may be made of the same materials or different materials which may include wood, steel, aluminum, fiberglass, glass, rigid plastics and the like.

A sampling apparatus 22 is attached to a vertical member 24 of the frame 14. The sampling apparatus 22 includes an inlet housing 26 fixedly attached to memliber 24, a moveable outlet housing 28 aid a filter media holder 30 disposed between the inlet housing 26 and the outlet housing 28. A clamping device 32, such as an over-center clamp provides a positive locking and compression arrangement for making a fluid-tight seal during a filtering operation. The clamping device 32 includes a first arm 34 rotatably attached at a first end 36 to the outlet housing 28 and a second arm 38 having a first end 40 attached to a handle 42. The distal end 44 of handle 42 is pivotally attached to the inlet housing 26 by means of an axle 46 that is linked by a spindle 48 to a distal end 50 of the first arm 34. Rotation of the handle 42 and second arm 38 about axle 46 causes the first arm to move outlet housing 28 vertically toward or away from tile inlet housing 26 thereby clamping or releasing media holder 30. As shown in FIG. 1, the clamping device 32 has two sets of first arms 34 and second arms 38, joined by handle 42 and pivotally attached to opposite sides of the inlet and outlet housings 26 and 28.

In order to more precisely align the inlet and outlet housings 26 and 28 for a fluid-tight seal, it is preferred to guide the outlet housing 28 during the clamping step along tracks, slide bars or guide rods 52 and 54. Housing movement stop lugs, such as lug 56 attached to rod 52, effectively limit the distance the second housing 28 can travel along rod 52. The rods 52 and 54 should be long enough, however, to allow sufficient spacing between housings 26 and 28 when inserting and removing the filter media holder 30.

Figure 2:
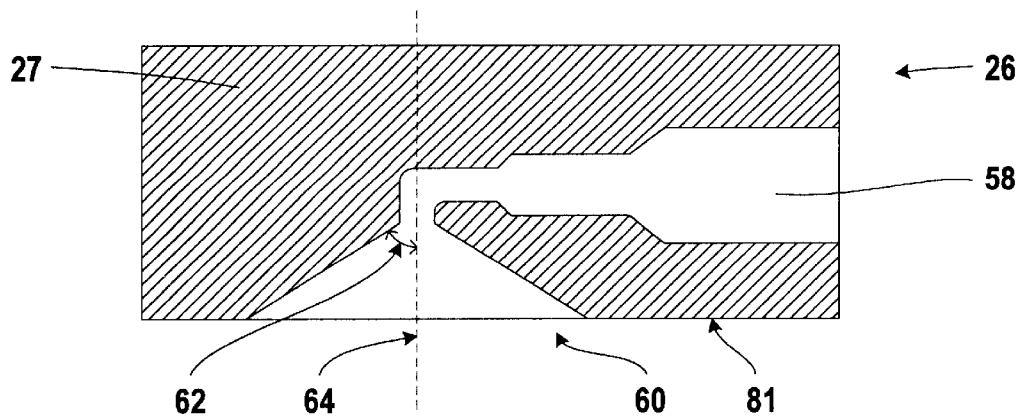
FIG. 2 is a cross-sectional view, not to scale, of an inlet housing for a sampling apparatus according to the invention.

Construction details of a preferred inlet housing are shown in cross-section in FIG. 2. The inlet housing 26 consists of a substantially rectangular cast or machined block 27 containing an inlet port 58 connected in flow communication with an inlet fluid cavity 60 which has a generally frustum conical shape. The side members of tile fluid cavity 60 preferably make an angle 62 of about 60° with a vertical axis 64 vertically through the fluid cavity 60. The cavity 60 preferably has a volume ranging from about 0.5 to about 5 milliliters.

Figure 3:
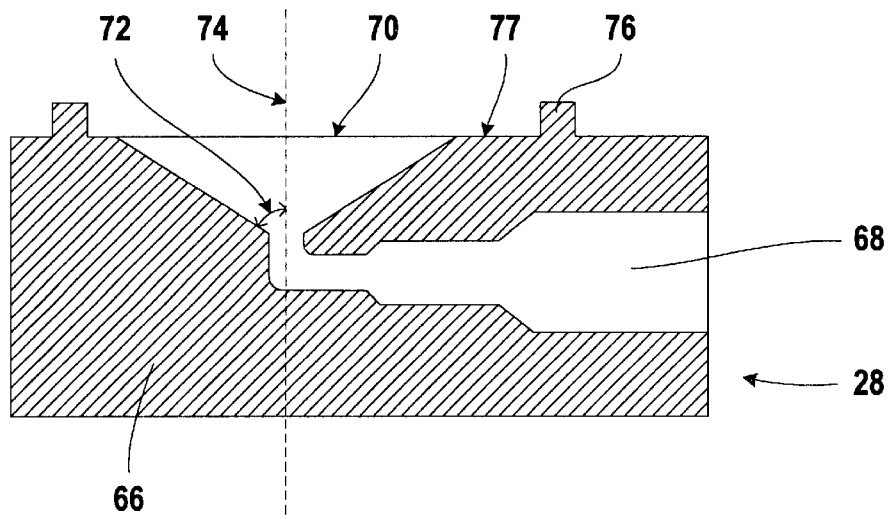
FIG. 3 is a cross-sectional view, not to scale, of an outlet housing for a sampling apparatus according to the invention.

A preferred outlet housing 28 is shown in cross-sectional in FIG. 3. The outlet housing 28, like the inlet housing 26, consists of a substantially rectangular cast or machined block 66 containing an outlet port 68 which is in fluid flow communication with a fluid collection cavity 70 which has a generally frustum conical shape. The side members of collection cavity 70 preferably make an angle 72 of about 60° with a vertical axis 74 through the collection cavity 70. Raised ledge 76 assists in locating and holding a sealing member for forming a fluid tight seal between the upper surface 77 of outlet housing 28 and the filter media holder 30.

Figure 4:
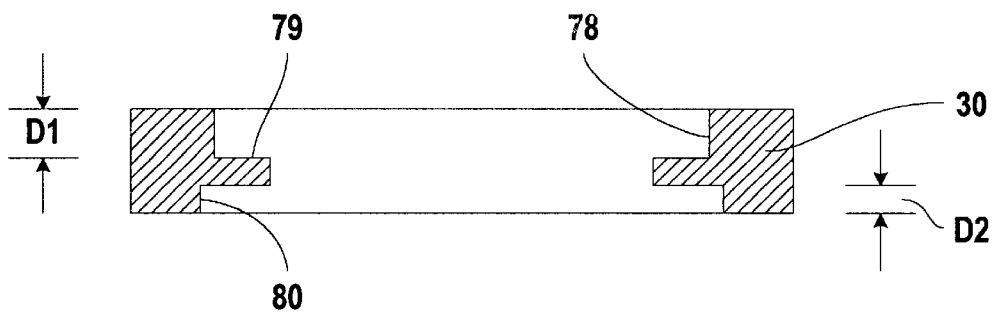
FIG. 4 is a cross-sectional view, not to scale, of a filter media holder for a sampling apparatus according to the invention.

A preferred filter media holder 30 is shown in a cross-sectional view in FIG. 4. The Filter media holder 30 is a substantially cylindrical holder which nay be machined or cast from a solid material such as aluminum, steel, plastic and the like. The holder 30 preferably has a thickness ranging from about 0.2 to about 0.5 inches and an outside diameter ranging from about 1 to about 2.0 inches. The holder has first and second annular recesses 78 and 80 respectively therein for support of filter media, filter media support screens and filter media sealing members. Details of the media, screen and sealing members are described in detail with reference to FIG. 6 below. Tile first annular recess 78 preferably has a diameter ranging from about 0.875 to about 1.125 inches and the second annular recess 80 preferably has a diameter ranging from about 0.95 to about 1.05 inches. The difference in diameter of the annular recesses assists in placing the holder 30 in the correct orientation between the inlet and outlet housing members 26 and 28. The depth D1 of annular recess 78 preferably ranges from about 3.5 to about 5.5 millimeters and the depth D2 of annular recess 80 preferably ranges from about 1 to about 3 millimeters. It is preferred that the depths D1 and D2 be sligthly less than the combined thicknesses of the sealing members, filter media and support screens so that there is sufficient compression of the sealing members between the inlet and outlet housings to form a fluid tight seal.

Figure 5:
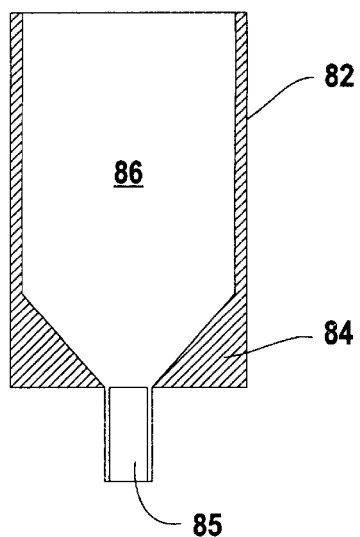
FIG. 5 is a cross-section view not to scale of an inlet sample reservoir for a sampling apparatus according to the invention.

Referring again to FIG. 1, filter patch samples are obtained for a fluid sample by introducing a fluid into fluid reservoir 82 which is attached to the upper L-shaped section 18 of frame 14. A cross-sectional view of fluid reservoir 82 is shown in FIG. 5 and includes a substantially cylindrical shell 84 defining a fluid cavity 86 which preferably has a fluid volume ranging from about 10 to about 100 milliliters in order to flow a fixed amount of fluid through the filter media when making the filter patches so that the concentration of particulate in the fluid may be determined. The fluid flows from the reservoir 82 through an outlet port 85 and through an inlet conduit 86 (FIG. 1) to the inlet port 58 of inlet housing 26 (FIG. 2).

Figure 6:
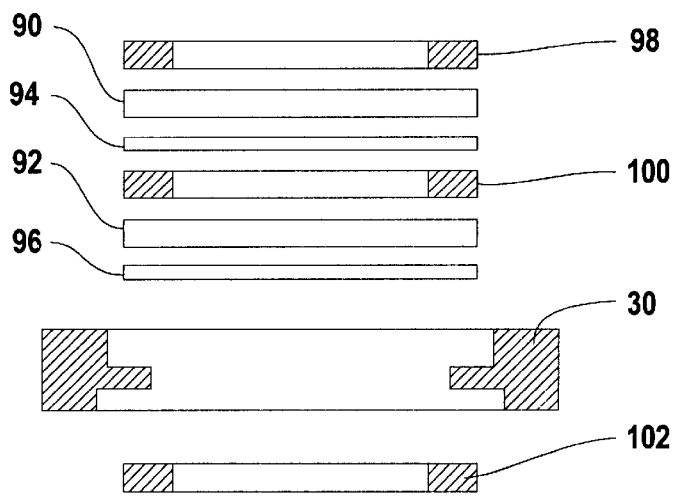
FIG. 6 is an exploded side view of sealing members, support members and filter media for a sampling apparatus according to the invention.

Details of the filter media, media support and sealing members are shown in FIG. 6. Preferred filter media 90 and 92 include, glass fiber, polymeric, paper or cellulosic filter paper having a wide range of pore size openings or particle size retention. in this regard it is particularly preferred to use filter media 90 having a pore size ranging from about 5 to about 30 microns, preferably from about 6 to 10 microns and filter media 92 having a pore size ranging from about 0.5 to about 20 microns, preferably from about 1 to about 5 microns.

Because the Filter media is typically relatively thin and flexible it is preferred to support the filter media with support screens 94 and 96. The support screens may be made of a variety of thin relatively rigid materials having a mesh size ranging from about 50 microns to about 50 millimeters. Materials for the support screens 94 and 96 include metals, plastics, fiberglass and the like. Particularly preferred support screens 94 and 96 are stainless steel screens having a thickness ranging from about 5 to about 15 mils and having openings therethrough ranging from about 50 to about 60 mils in diameter.

In order to form a fluid tight seal between the filter media 90 and 92 and the media holder 30, and between the holder 30 and the inlet housing 26, sealing members 98 and 100 are used. The sealing members 98 and 100 are preferably elastomeric materials selected from fluoropolymer or synthetic rubber. Each of the sealing members 98 and 100 have a thickness ranging from about 2 to about 3 millimeters and a diameter ranging from about 20 to about 60 millimeters such that the sealing members 98 and 100 sealingly engage the media and support screen within annular recess 78 in media holder 30 (FIG. 4). Sealing member such as 98 also seals against tile surface 81 of inlet housing 26 (FIG. 2).

An elastomeric o-ring or gasket 102 is preferably inserted in annular recess 80 to seal between the media holder 30 and surface 77 of outlet housing 28. In this regard, it is particularly preferred that the side walls of annular recess 80 circumscribe raised ledge 76 of outlet housing 28 and so that gasket 102 is retained within the inner circumference of raised ledge 76. The thickness of sealing member 102 preferably ranges from about to about 2 to about 3 millimeters and the diameter thereof preferably ranges from about 20 to about 60 millimeters. While it is preferable to position the sealing 21 members 98, 100 and 102 within the recesses 78 and 80, they may be placed elsewhere according to the defined function thereof, namely, forming seals between the media holder 30 and the housings 26 and 28.

After passing through the filter media, the fluid exits the outlet housing 28 through outlet port 68 (FIG. 3) and outlet conduit 88 (FIG. 1). Inlet and outlet conduits 86 and 88 may be any suitable material including rigid tubes or flexible hoses. The fluid may be caused to flow from the reservoir 82 through the inlet and outlet housings 26 and 28 and filter media 90 and 92 by gravity or preferably by applying a reduced or subatmospheric pressure to the fluid flow path by connecting a vacuum pump to outlet conduit 88. If a vacuum pump is used, it is preferred to use a pulp which has a flow volume of at least about 10 scfm in order to draw the sample through the apparatus in a relatively short period of time. Typically, the entire fluid sample is preferably drawn through the filter media in no more than about 120 seconds.

Figure 7:
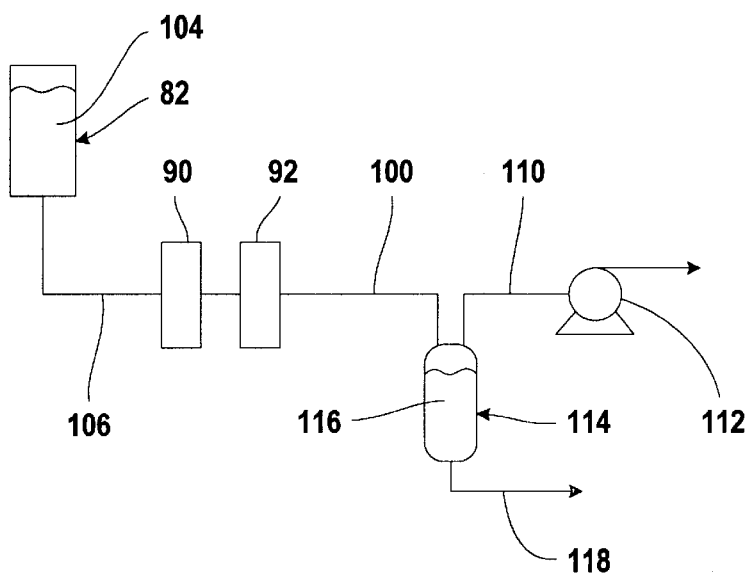
FIG. 7 is a simplified schematic flow diagram of a process for making filter patch samples according to the invention.

A simplified schematic flow diagram of a dual filter patch apparatus including dual filter media is shown in FIG. 7. Fluid 104 is introduced into fluid reservoir 82 and is caused to flow through filter media 90 and 92 through conduits 106, 108 and 110 by applying a reduced pressure to the conduits 106, 108 and 110, filter media 90 and 92 and fluid reservoir 82 by action of a vacuum pump 112. In order to prevent liquid from flowing into the vacuum pump 112, a liquid entrainment vessel or knock-out pot 114 is used to capture liquid 1 16 which may be drained therefrom through drain conduit 118.

Once a predetermined amount of fluid has been drawn through the filter media, the filter media 90 and 92 may be rinsed with water or a solvent to remove traces of the fluid from the media. The media holder 30 containing the filter patch samples is then removed from between the inlet and outlet housings 26 and 28 by rotating handle 42 so that outlet housing 28 moves vertically away from inlet housing 26 along slide rods 52 and 54 (FIG. 1) as shown in FIG. 8. The Filter media 90 and 92 containing captured particulate from the fluid may be separated from the sealing members 98 and 100 and support screens 94 and 96 (FIG. 6) and dried. The amount and size distribution of particles captured by the filter media 90 and 92 may be determined for a fixed volume of fluid by any conventional optical or visual techniques.

As shown in FIG. 8, as the handle 42 is rotated in a clockwise direction, the outlet hosing 28 moves vertically downward along slide rod 52. As the housing 28 moves downward, the conduit 88 connected to the outlet port 68 of the housing 28 also moves downward. In order to permit the conduit 88 to moved, it is preferred that the vertical flame member 24 contain a slotted opening 120 (FIG. 9) for movement therein of conduit 88 during rotation of handle 42. Circular slot 122 in frame member 24 provides an opening for conduit 86 attached to outlet port 85 of reservoir 82.

The device as described above may be used to make a single filter patch sample or to make two filter patch samples essentially simultaneously thereby reducing the time required to prepare multiple samples having a different range of particulate retention. In this regard it is preferred to use a larger pore filter paper 90 in the upper position of the filter media stack (FIG. 6) and a smaller pore filter paper 92 in the lower position of the filter media stack. This arrangement provides a means for more effective flow through the filter media so that the time required to prepare the filter patch samples is minimized.

In yet another aspect of the invention, various techniques may be used in combination with the above described device for identifying the type of particles in a fluid sample and determining their size distribution and concentration. A method for identifying the type of particles deposited on a substrate using optical colored filters is described, for example, in U.S. Pat. No. 4,047,814 to Westcott, incorporated herein by reference as if fully set forth.

Other methods for determining the identity, concentration and particle size distribution of particulate or contaminants in a fluid include preparing standard filter patch samples containing known particulates of known size distribution and/or concentration and comparing the standards to filter patch samples made from a fluid to be analyzed. lie comparison of the filter patch samples and standard filter patch samples may be made with the unaided eye, by use of a microscope, microscopic comparison with standard photographs or by using electronic image analysis techniques. Filter patch samples made according to the invention may also be compared by use of a weighing balance, an x-ray fluorescence spectroscopy device, magnetometer device, Hall effect flux analyzer, atomic emission spectrometer, or other devices suitable for analysis of different types of particulate material. In addition, the particulates on the filter patch samples may be re-suspended in a solution and the solution passed through an in-line optical contamination meter or the re-suspended particles may be chemically treated or reacted with solvents or other chemical reagents.

A particularly preferred use of the device according to the invention is to determine the quantity and/or size distribution of ferrous particles in a fluid sample. One method for determining such particle size and concentration is to first isolate the ferrous particles from the fluid sample such as by stirring the sample in the fluid reservoir 82 with a magnetic rod to remove the ferrous particles from the fluid before filtering the fluid sample through the filter media in media holder 30. The remaining fluid and particles are then filtered through the media as described above and the particles concentration, size distribution and identity may determined as by a variety of techniques including the methods set forth in U.S. Pat. No. 4,047,814 to Westcott.

The ferrous particles attached to the magnetic rod are then reslurried in an appropriate fluid and placed in the fluid reservoir 82 for filtering through fresh filter media in media holder 30. Tile resulting filter patches may be analyzed by well known techniques to determine the size distribution and concentration of ferrous particles which were in the original fluid sample.

While the invention has been described in detail, it is to be expressly understood that various changes of form, design or arrangement may be made to the invention by those skilled in the relevant art without departing from the spirit and scope of the invention. Therefore, the above mentioned description is to be considered exemplary, rather than limiting, and the scope of the invention is defined by the following claims.

What is claimed is:

1. A method for determining quantitative or qualitative properties of particulate in an oleaginous material, comprising:

providing an oleaginous fluid sample, feeding the fluid sample to a fluid sample holder having a defined volume in flow communication with a dual filter patch device containing first and second porous media, extracting ferrous particles from the fluid sample in the fluid sample holder to provide a ferrous particle free fluid and extracted ferrous particles, applying a reduced pressure to the filter patch device to draw the ferrous particle free fluid sequentially through the porous media, removing residual ferrous particle free fluid from the porous media using a solvent for the fluid, and optically observing particulate material on the porous media.

2. The method of claim 1 further comprising drying the porous media after removing residual ferrous particle free fluid therefrom.

3. The method of claim 1 wherein the first porous medium has a pore size ranging from about 6 to about 10 microns in diameter and the second porous medium has a pore size ranging from about 1 to about 5 microns in diameter.

4. The method of claim 1 further comprising physically comparing the particulate matter deposited on the first and second porous media in order to determine a particle size distribution thereof.

5. The method of claim 1 further comprising physically comparing the amount of particulate matter deposited on the first and second porous media in order to determine tile amount of particulate contamination in the oleaginous material.

6. The method of claim 1 further comprising suspending the extracted ferrous particles in an appropriate carrier fluid after drawing the ferrous particle free fluid through the porous media to provide a mixture of ferrous particles and carrier fluid, feeding the mixture of carrier fluid and extracted ferrous particles to the fluid sample holder of the filter patch device containing fresh porous media, and applying a reduced pressure to the filter patch device to draw the mixture of carrier fluid and extracted ferrous particles through the porous media.

* * * * *